(12) United States Patent
Gerard et al.

(10) Patent No.: US 8,172,756 B2
(45) Date of Patent: May 8, 2012

(54) ULTRASONIC IMAGING SYSTEM AND METHOD

(75) Inventors: Olivier Gerard, Viroflay (FR); Odile Bonnefous, Rueil-Malmaison (FR); Pascal Allain, Saint Cyr l'Ecole (FR); Eric Denis, Yerres (FR); Eric M. G. JP. Saloux, Saint Manvieu-Norrey (FR); Cécile A. M. Marboeuf, Sèvres (FR)

(73) Assignee: Koninklijke Philips Electronics N.V., Eindhoven (NL)

( * ) Notice: Subject to any disclaimer, the term of this patent is extended or adjusted under 35 U.S.C. 154(b) by 945 days.

(21) Appl. No.: 12/089,931

(22) PCT Filed: Oct. 20, 2006

(86) PCT No.: PCT/IB2006/053865
§ 371 (c)(1),
(2), (4) Date: Aug. 6, 2008

(87) PCT Pub. No.: WO2007/046074
PCT Pub. Date: Apr. 26, 2007

(65) Prior Publication Data
US 2009/0219301 A1      Sep. 3, 2009

(30) Foreign Application Priority Data
Oct. 20, 2005 (EP) .................................... 05300840

(51) Int. Cl.
*A61B 8/00* (2006.01)
*A61B 8/14* (2006.01)

(52) U.S. Cl. ........ 600/450; 600/437; 600/443; 382/128; 382/107; 382/154

(58) Field of Classification Search .................. None
See application file for complete search history.

(56) References Cited

U.S. PATENT DOCUMENTS 7,343,031 B2 * 3/2008 Pedrizzetti et al. ........... 382/128
2002/0072674 A1 * 6/2002 Criton et al. .................. 600/454

OTHER PUBLICATIONS

Suhling M., et al., "Bimodal Myocardial Motion Analysis From B-mode and Tissue Doppler Ultrasound," Biomedical Imaging: Macro to Nano, 2004. IEEE International Symposium on Arlington, VA, USA Apr. 15-18, 2004. Piscataway, NJ, USA, IEEE, Apr. 15, 2004 pp. 308-311, XP010773859.
Suhling, M., "Myocardial Motion and Deformation Analysis from Echocardiograms," [online] Jul. 16, 2004, Swiss Federal Institute of Technology Lausanne, EPFL, Lausanne, CH, XPOOS4S0085 Retrieved from the Internet: URL: http://bigwww.epfl.ch/publications/suhling0404.html> p. 77-p. 98.

* cited by examiner

*Primary Examiner* — Long V. Le
*Assistant Examiner* — Farshad Negarestan
(74) *Attorney, Agent, or Firm* — W. Brinton Yorks, Jr.

(57) ABSTRACT

The present invention relates to an ultrasonic imaging system for evaluating and displaying a deformation of a body organ. A sequence of image data sets comprising at least a first image data set and a second image data set of echographic data is acquired. A motion vector field is calculated between image points of the second image data set and image points of the first image data set. A reference point is chosen within or outside the first and second image data sets. A first scanline is defined, which comprises said reference point. A motion vector of an image point is projected onto the defined first scanline, which provides a projected tissue velocity along the first scanline. The projected tissue velocity is used for evaluating a ID component of a deformation of the body organ at the image point along the direction of the first scanline. Such a ID component of a deformation of the body organ, for example a strain rate or a strain, is further rendered in a graphical representation of the sequence of image data sets.

11 Claims, 8 Drawing Sheets

ULTRASONIC IMAGING SYSTEM AND METHOD

FIELD OF THE INVENTION

The present invention relates to an ultrasound imaging system for evaluating and displaying tissue deformation. The invention further relates to an imaging method to be used in such a system. The invention finally relates to a computer program for carrying out such an imaging method.

The invention finds its application in particular in the domain of echocardiographic imaging.

BACKGROUND OF THE INVENTION

In many diagnostic evaluations of ultrasonic images, a quantitative evaluation of the tissue's kinematic properties (velocity and deformation) improves the ability to identify dysfunctions. This kind of analysis has a particular relevance in the field of echocardiographic imaging. In this field, the assessment of the effective ventricular function requires a knowledge of numerous properties about the ventricular dynamics. A technique for evaluating velocity is known as Tissue Doppler Imaging (TDI), which allows the measurement of tissue velocity over all points in the ventricular wall. The measurement of tissue velocity helps to uncover abnormalities which are not immediately observable from tissue visualization in B-mode imaging. The measured tissue velocity provides information about rigid body displacement and contraction/distension. The contraction/distension is related to the myocardial activity. Additional features such as local strain or strain rate of the tissue can be derived from the tissue velocities.

A drawback of TDI is that only a component of tissue velocity along a scanline can be measured. Therefore, when tissue moves in a direction that is not aligned with the scanline, the Doppler velocity does not reflect the effective tissue kinematics. Only the components of strain and strain rate along the scanline can be evaluated, giving a reduced view of the local deformation state. Moreover, this limits the application of TDI to the anatomical sites that can either be imaged aligned along a scanline or that have a displacement in the direction of the scanline. In echocardiography, these anatomical sites correspond essentially to the interventricular septum and to the lateral walls in apical view.

Another consequence is that several scanlines should be acquired at the same location for TDI acquisitions, which means that the spatial resolution, i.e. the number of scanlines, is reduced if a high acquisition frame rate is to be achieved.

United State Patent Application number US2005/0070798 discloses a method of estimating tissue velocity vectors and oriented strain from a single acquisition of B-mode ultrasonic imaging data. An optical flow velocity field estimation technique is applied for providing a dense motion vector field from a sequence of at least two successive B-mode image frames without the need to acquire more image data in the Doppler mode. An evaluation of strain and strain rate data in any direction, even transverse to the scanline, can be derived from the calculated dense motion vector field. A drawback of such a method is that it does not provide any solution for visualizing the evaluated tensors of strain and strain rate data, which would be convenient for the user.

SUMMARY OF THE INVENTION

It is an object of the invention to provide a system for and a method of producing and visualizing components of tissue velocity and strain derived from the calculation of a dense motion vector field in a way which is convenient for the user.

This is achieved by a system in accordance with the invention for evaluating and displaying a deformation of a body organ, said system comprising:

means for acquiring a sequence of image data sets comprising at least a first image data set of echographic data and a second image data set of echographic data from said body organ by transmitting ultrasonic beams against said body organ and receiving corresponding beams reflected by said body organ;

means for calculating motion vectors corresponding to image data points of said sequence of image data sets between said second image data set and said first image data set, said image data point being located by coordinates within a referential of said first and second sequences of image data sets;

means for selecting a reference point within said referential;

means for projecting the motion vector corresponding to an image data point to a first scanline which links said image data point to said reference point, said means being configured to generate a projected tissue velocity value of said image data point;

means for evaluating a deformation of said body organ at said image data point from said projected motion value; and means for producing and displaying a graphical representation of said evaluated deformation.

With the invention, a sequence of at least two two-dimensional or three-dimensional image data sets is acquired. A dense motion vector field is calculated as an estimation of tissue velocities of image points of the second image data set with respect to the first image data set. A reference point is chosen within a referential of the second image data set. This reference point is used as a starting point for defining a first scanline. This first scanline is further used for evaluating a 1D component of a deformation of the body organ along the directions of the first scanline. The reference point may be placed either outside or inside the image data set.

A projected tissue velocity value is obtained by projecting the motion vector calculated for the image data point on the first scanline comprising said reference point. An evaluation of a 1D component of the deformation of the body organ is derived from this projected motion value. Such a 1D component of the deformation is, for example, the strain rate, which evaluation is based on the spatial gradient of the projected tissue velocity value or the strain, which is obtained by integrating the strain rate over time. The strain and strain rate are one-dimensional data, which are further rendered in a graphical representation, for example as a color-encoded information superimposed on a grey-level ultrasonic 2D or 3D image.

With the invention, only a projection of the tissue deformation and not the whole tensor of deformation is evaluated and displayed at a time, which allows the production of a graphical representation which is easy to read and to analyze. As a matter of fact, such a graphical parametric representation is very familiar to the user.

Preferably, a sequence of 3D image data sets is acquired.

In a first embodiment of the invention, a single reference point is selected for all the image data points. The motion vectors are projected along scanlines which may be compared to acquisition scanlines of a real probe. Advantageously, the reference point is placed outside the image data set, preferably at possible locations of the probe used for acquiring the sequence of image data sets. The deformation values are evaluated along these scanlines. An advantage of the first embodiment in accordance with the invention is that its reproduces the kind of graphical representation which can be obtained by using TDI and with which the user is familiar.

In a second embodiment of the invention, a second scanline is defined which is perpendicular to the first scanline. The ultrasonic imaging system in accordance with the second embodiment of the invention comprises means for projecting the motion vector to the second scanline. Therefore, a second 1D projected motion value is obtained which is perpendicular to the one obtained by projection of the motion vector to the first scanline. A second component of the deformation can be derived. For example, the first scanline is the long axis of the heart and the second scanline is a short axis of the heart. An advantage of the fourth embodiment of the invention is to provide a 2D evaluation of the local deformation of the body organ. This is more realistic, in particular for the heart, which is known to undergo a deformation along three main directions. The first scanline may provide an evaluation of the longitudinal deformation and the second scanline an evaluation of the radial deformation.

In a third embodiment of the invention, a view plane is defined which comprises the chosen reference point. The projections of the motion vectors are performed within the view plane and not in the entire 3D image data set. The generated graphical representation may advantageously superimpose the color-encoded deformation value on the 2D grey-level image frame corresponding to the defined view plane. An advantage for the user is that with such a 2D graphical representation there is no need to navigate within a volume of data.

Advantageously, anatomical reference points are used for defining the view plane. Consequently, the view plane may correspond to a view which can really be scanned by an ultrasonic probe such as, for example, a long-axis parasternal view. In this particular case, the anatomical reference points are the apex and the heart's long axis.

In a fourth embodiment of the invention, the projection of the motion values and the evaluation of the tissue deformation are not carried out within the entire view plane, but in a region of interest defined within the view plane. As a matter of fact, there may be regions in the view plane in which the tissue velocity information is not relevant. This is the case, for example, in chamber cavities of the heart which are filled with blood. By contrast, the myocardial wall is a region of great interest. Therefore, a region of interest is delimited between a first and a second border of the body organ. Advantageously, the endocardial walls and the epicardial walls are automatically segmented. An advantage is that only relevant information is calculated and that computation cost is saved.

In a fifth embodiment of the invention, the reference point is chosen inside the 3D image data sets. This allows the definition of a view plane which could not be scanned by an ultrasonic probe. In particular, a relevant view plane is a view plane which is defined by the reference point placed on the long-axis of the heart and chosen perpendicular to the long-axis. This view plane is preferably chosen above the mitral valves. Such a short-axis view plane cannot be scanned by an ultrasonic probe. In this short-axis view plane, the defined first scanlines are radial with respect to the long axis of the heart, and therefore the projections of the tissue velocity motion vectors provide a radial component of the tissue velocity. Such a radial component of the tissue velocity cannot be measured with the TDI technique, because it is perpendicular to the scanlines fired by the ultrasonic probe and because the ultrasonic probe usually cannot be placed inside the left ventricle of the heart.

An evaluation of the radial component of the tissue deformation is derived. This is of great interest, because this radial component of the tissue deformation has a physiological correspondence. As a matter of fact, the contraction forces of the myocardial walls are usually decomposed into a longitudinal, a circumferential, and a radial component. Therefore, an advantage of the fifth embodiment of the invention is that it allows a calculation of the projected tissue velocities and an evaluation of 1D tissue deformations from a reference point location at which it is not possible to place a real probe.

In a sixth embodiment of the invention, a second graphical representation is generated from a second reference point and, advantageously, a second view plane. From this second reference point, a second set of 1D components of the deformation can be obtained from the previously calculated motion vectors simply by recalculating new projected motion values and deformation values from said second reference point. It should be noted that this sequence of operations can be repeated as many times as required. An advantage is that the system in accordance with the fifth embodiment allows the generation of a plurality of graphical representations of 1D components of the deformation of the body organ from a single ultrasonic acquisition. These 1D components of the tissue deformation, for example the radial, longitudinal, and circumferential components of the heart deformation, can advantageously be visualized at the same time.

In a seventh embodiment of the invention, a specific reference point is selected for an image data point for which a motion vector has been calculated. A curved line is designed to comprise the reference points corresponding to the image data points. The reference point corresponding to an image point is selected on the curved line such that the first scanline linking the image data point to the reference point is perpendicular to a tangent of said curved line at said reference point.

An advantage of the seventh embodiment of the invention is that a curved line can be selected which follows anatomical structures and, for example, follow the shape of the region of interest delimited by the first and second borders.

The present invention also relates to the imaging method to be used in such an ultrasonic imaging system.

These and other aspects of the invention will be apparent from and will be elucidated with reference to the embodiments described hereinafter.

BRIEF DESCRIPTION OF THE DRAWINGS

The present invention will now be described in more detail, by way of example, with reference to the accompanying drawings, wherein.

DETAILED DESCRIPTION OF THE INVENTION

The invention relates to an ultrasonic imaging system for evaluating and representing a deformation of a body organ from an acquisition of 2D or 3D echographic data. In the following the system in accordance with the invention will be described in more detail in the particular domain of echocardiography, for evaluating and representing a deformation of the myocardial wall of the heart of a patient from a single acquisition of 3D echographic data.

Figure 1:
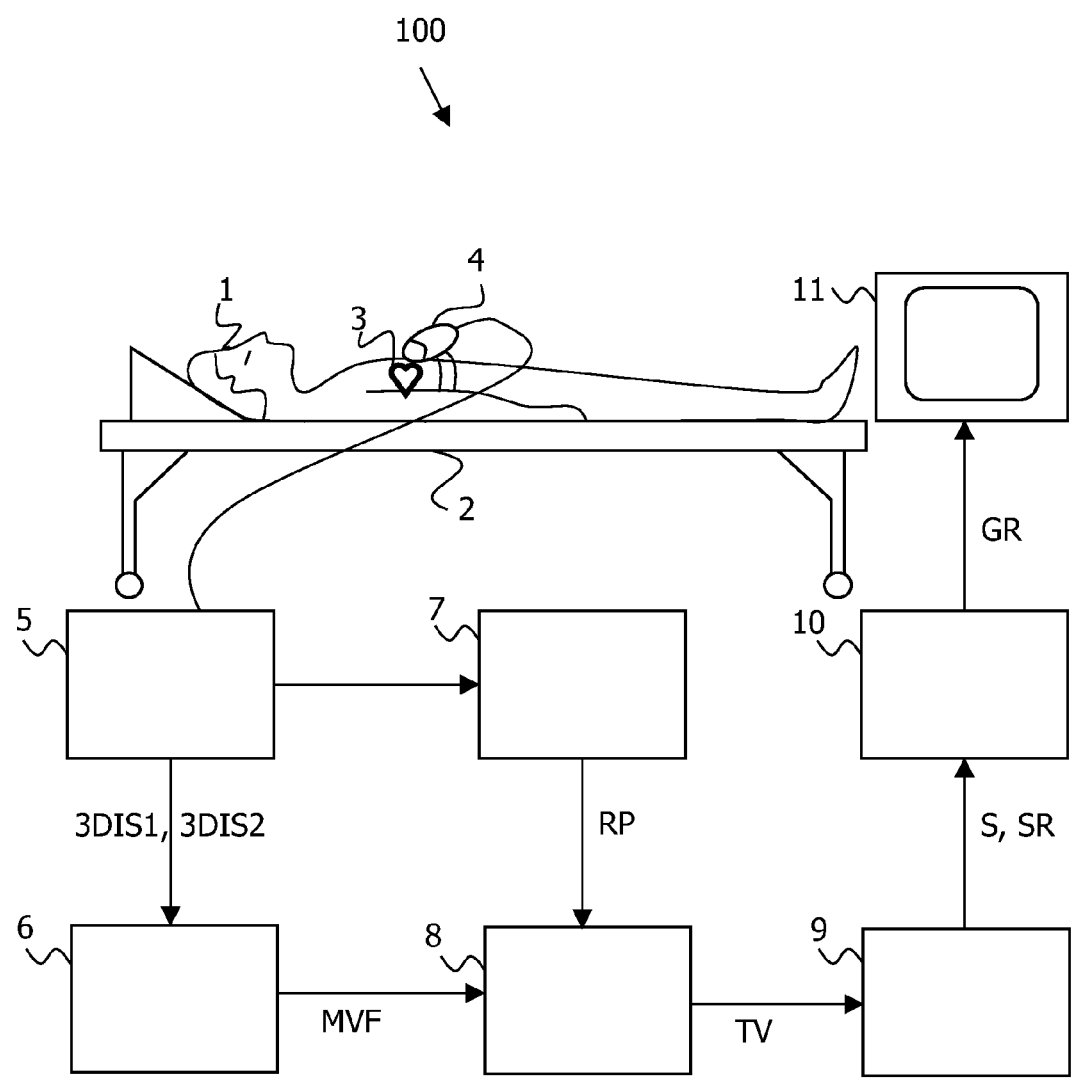
FIG. 1 is a schematical drawing of a system in accordance with the invention.

However, the invention is not limited to echocardiography and may be applied to the evaluation of the deformation of any body organ that can be imaged by ultrasound. The schematical drawing of FIG. 1 shows an ultrasonic imaging system 100 in accordance with the invention. A patient 1 is arranged on a patient table 2. His symbolically indicated heart 3 is pointed by an ultrasonic probe 4. The ultrasonic probe 4 comprises a 2D transducer array which is adapted to transmit ultrasonic beams against the heart 3 of the patient 1 and to receive corresponding echographic beams reflected by said heart. The system 100 in accordance with the invention comprises means 5 for generating a sequence of at least two 3D image data sets of the heart 3 $3DIS_1$ and $3DIS_2$ from said received echographic beams. It should be noted that an image data set either comprises raw data or a scan converted image. The at least two 3D image data sets advantageously correspond to successive time instants of the cardiac cycle. A 3D image data set is a volume of image data points which can be identified by triplets (x, y, z) of coordinates within a referential (O, X, Y, Z) of the 3D image data sets.

The system in accordance with the invention further comprises means 6 for calculating motion vectors $\vec{MV}$ corresponding to image data points of the sequence of 3D image data sets between the second 3D image data set $3DIS_2$ and the first 3D image data set $3DIS_1$. A dense motion vector field MVF is obtained, which comprises a calculated vector of 3D motion components $$\vec{MV} = \begin{pmatrix} V_x \\ V_y \\ V_z \end{pmatrix}$$

for at least each image data point of the second 3D image data set $3DIS_2$. Known techniques such as optical flow or block matching are used.

The system in accordance with the invention further comprises means 7 for selecting a reference point RP within said referential (O, X, Y, Z) of the second sequence of 3D image data sets $3DIS_2$. Considering the motion vector $\vec{MV}$ corresponding to an image data point IP, said reference point RP is further used for defining a first scanline SL1 which comprises said reference point RP. The system in accordance with the invention further comprises means 8 for projecting the motion vector $\vec{MV}$ to the first scanline SL1, as shown in FIG. 3B. A projected tissue velocity value TV is obtained, which represents a 1D component of the motion vector along the first scanline SL1.

It should be noted that the reference point RP may either be selected once for all image data points of the image data set or be specifically selected for each image data point, as will be explained in more detail below.

The projected tissue velocity value TV represents an evaluation of a local tissue velocity and is further used by means 9 for evaluating a deformation of the tissue of the body organ at said image data point IP. To this end, image processing techniques well known to those skilled in the art are used. In particular, a strain rate value SR of the deformation at the image data point IP is evaluated by calculation of a spatial gradient of the projected motion value PMV. Advantageously, a strain value S is also estimated as an integration over time of the strain rate value SR. Therefore, the evaluated strain and strain rate values S, SR of the tissue at the image data point IP are also 1D components of the deformation along the scanline SL.

This 1D component of the deformation is further rendered on a graphical representation GR of the sequence of 3D image data sets by display means 10. Advantageously, said display means are adapted to encode the evaluated deformation values in accordance with a range of colors and to superimpose them on the grey-level sequence of 3D image data sets.

It should be noted that, in the case of a sequence comprising more than two 3D image data sets and, in particular, covering a complete cardiac cycle, the means 6 for calculating motion vectors can be repetitively applied to couples of successive 3D image data sets, leading to a plurality of motion vector fields. Thus a plurality of sets of 1D components of the deformation can be evaluated from the plurality of motion vector fields. An advantage is that an evolution of the deformation of the body organ, for example the myocardium, can be observed during the cardiac cycle.

Figure 2:
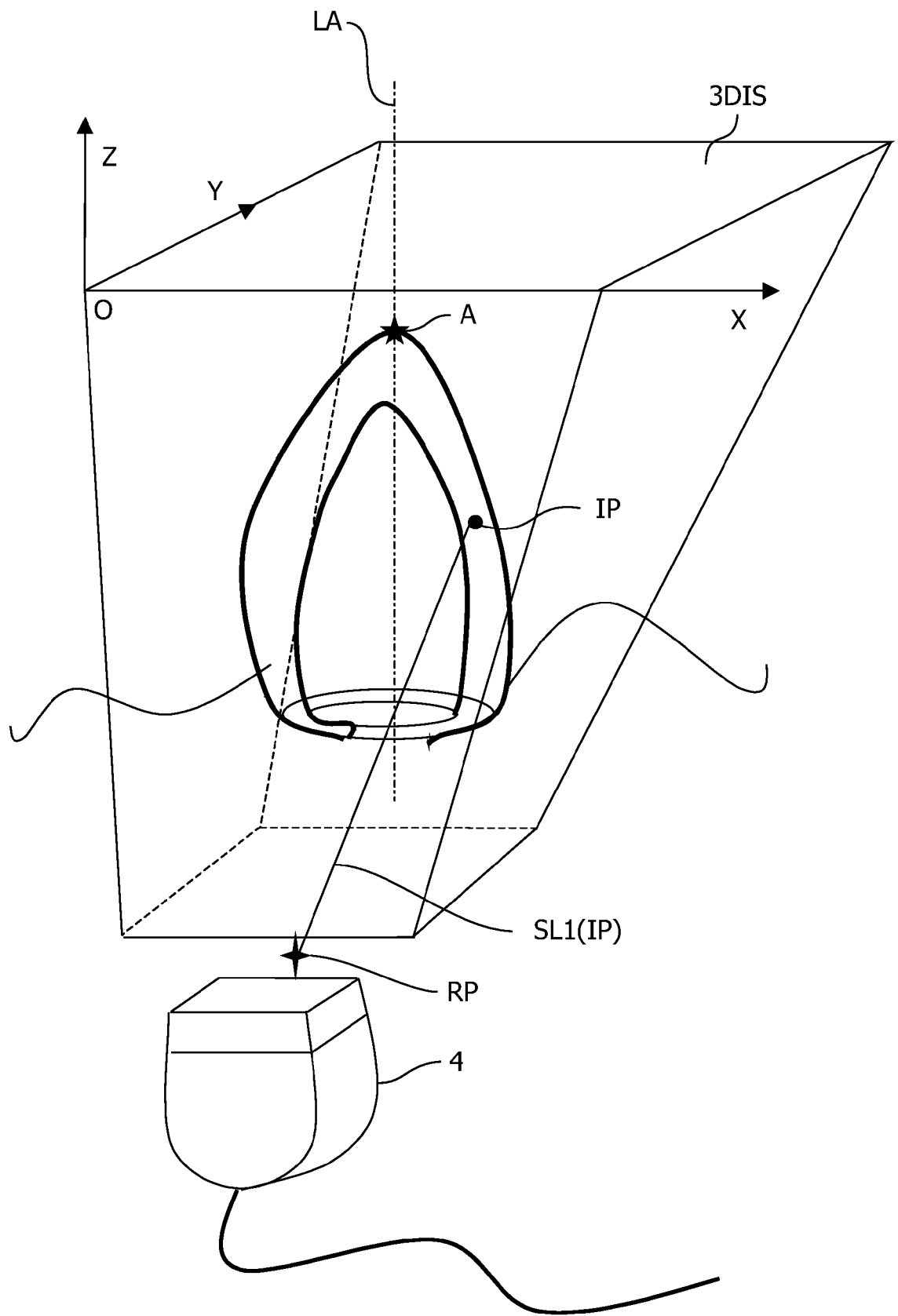
FIG. 2 is a schematical drawing of a 3D image data set acquired by the acquisition means in accordance with the invention.

The schematical drawing of FIG. 2 shows a 3D image data set 3DIS that has been acquired by the acquisition means 5. Such an image data set comprises echographic data of the heart, and in particular of the myocardium. As was noted above, the 3D image data set 3DIS comprises image data points IP (x, y, z), which are located by their coordinates in a referential of the 3D image data set (0, X, Y, Z). The heart is usually identified by anatomical reference points such as the apex A or the longitudinal axis of the heart LA. These anatomical reference points are also located by coordinates in the referential (O, X, Y, Z).

Figure 3A:
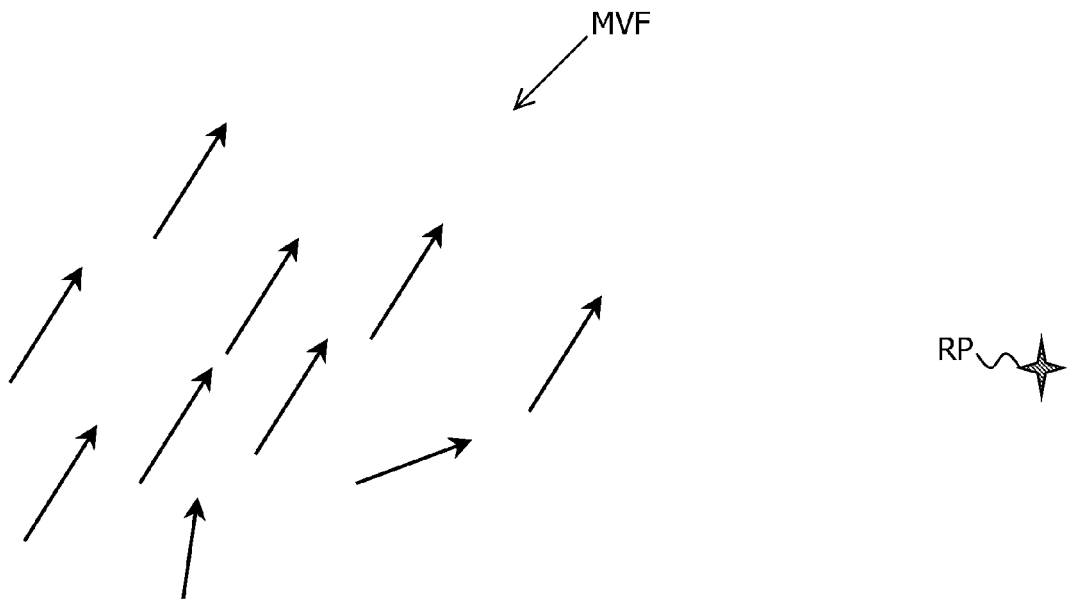
FIGS. 3A and 3B are schematical drawings of a motion vector field and corresponding projected tissue velocity values in accordance with the first embodiment of the invention.
Figure 3B:
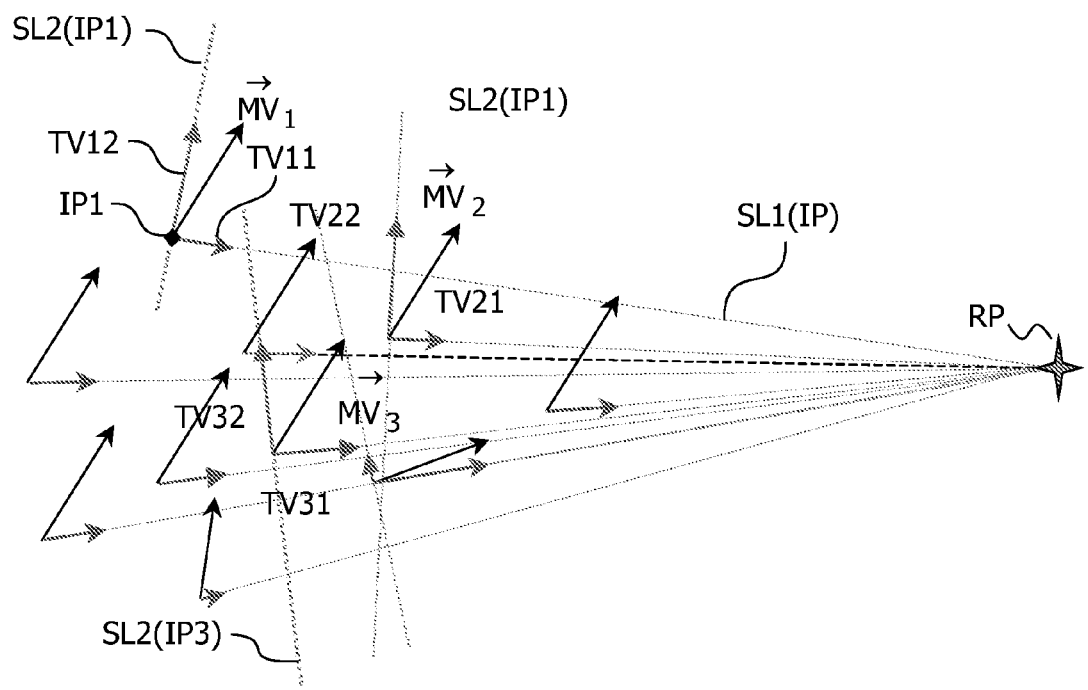

The schematical drawing of FIG. 3A shows the dense motion vector field MVF calculated by the means 6. Advantageously, optical flow methods well-known to those skilled in the art, are involved. These optical flow methods are based on the assumption of conservation of brightness. According to this assumption, an object moves from one image frame to another without local change of its brightness.

Referring to FIG. 3B, the reference point RP is chosen either inside or outside the image data set. Considering the image data point IP1 of the 3D image data set 3DIS, a first scanline SL1(IP1) is drawn which links the reference point RP to the image data point IP1. The means 8 for projecting the motion vector $\vec{MV}_1$ corresponding to the image data point $IP_1$ to the first scanline $SL_1(IP1)$ is adapted to provide a projected tissue velocity value $TV_1$ along the direction of the first scanline $SL_1(IP1)$.

In a first embodiment of the invention, a single reference point RP is selected for all the image data points $IP_i$ of the image data set, where i is an integer. A beam of scanlines $SL_1(IP_i)$ is thus obtained which can be considered as fired by a virtual probe located at the position of the reference point RP into the body organ.

Figure 4:
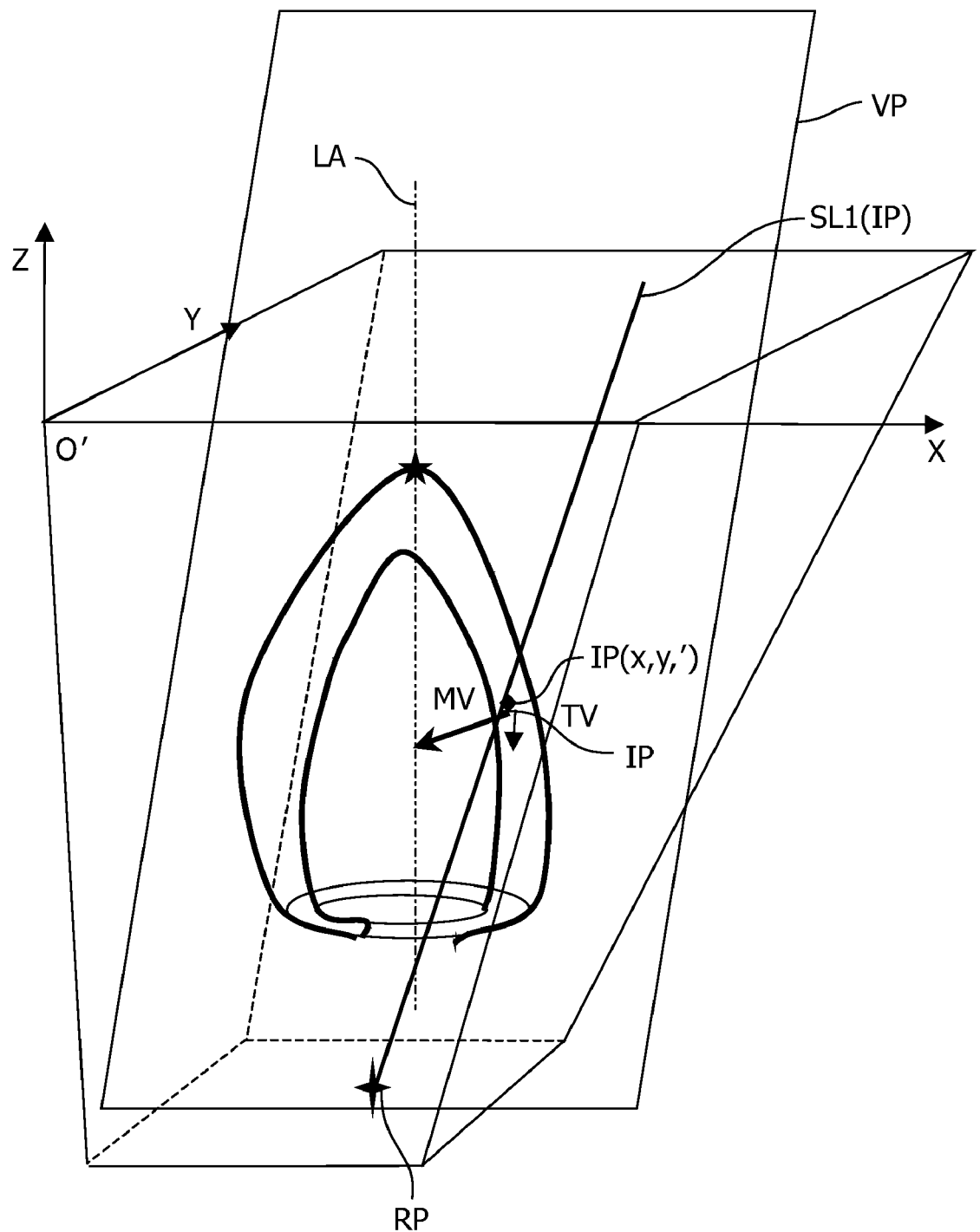
FIG. 4 is a schematical drawing of a view plane in accordance with the second embodiment of the invention.

Referring to FIG. 4, the reference point RP is advantageously chosen outside the image data set 3DIS. It should be noted that the reference point RP may alternatively be chosen so as to lie inside the 3D image data set 3DIS.

In a second embodiment of the invention, a second scanline $SL_2$ is defined, which is perpendicular to the first scanline $SL_1$, as shown in FIG. 3B. In FIG. 3B, the motion vector $\vec{MV}_1$ is projected to the second scanline $SL_2(IP_1)$ corresponding to the image data point $IP_1$, the motion vector $\vec{MV}_2$ is projected to the second scanline $SL_2(IP_2)$ corresponding to the image data point $IP_2$, and so on. Each image data point has its own second scanline. Projected tissue velocities $TV_{12}, TV_{22}, TV_{32}$ corresponding to the image data points $IP_1$, $IP_2$, $IP_3$ are obtained, which are 1D components of the tissue velocity along the respective second scanlines $SL_2(IP_1)$, $SL_2(IP_2)$, $SL_2(IP_3)$. A second component of the deformation $S_{i2}$, $SR_{i2}$ along the second scanline $SL_2(IP_i)$, where i is an integer belonging to $\{1,2,3\}$, can be derived.

An advantage of the second embodiment of the invention is to provide a 2D evaluation of the local deformation of the body organ. This is more realistic, in particular for the heart, which is known to undergo a deformation along three main directions. The first scanline may provide an evaluation of the longitudinal deformation and the second scanline an evaluation of the radial deformation.

In a third embodiment of the invention, a view plane VP is chosen within the 3D image data set. The view plane VP comprises the reference point RP. Projections TV of the motion vectors $\vec{MV}$ of the motion vector field are performed by the means 8, preferably for the image data points included within the view plane VP. The corresponding tissue deformations are derived by the means 9, thus providing a plane of strain and strain rate values S, SR. An advantage of the second embodiment of the invention is that the obtained set of 1D deformation values can be displayed, for example, by superimposition on the grey-level values of a 2D image frame corresponding to the view plane. Such a graphical representation is easier to analyze than a volume of image data through which the user should navigate.

Advantageously, the view plane may be defined by using anatomical reference points such as the apex A and the long axis LA of the heart. In this way the defined view plane corresponds to a view which could have been acquired by a real probe such as, for example, the long-axis apical view shown in FIG. 4. An advantage is that the user is provided with a graphical representation of the deformation corresponding to a view of the body organ that he usually analyzes.

Figure 5A:
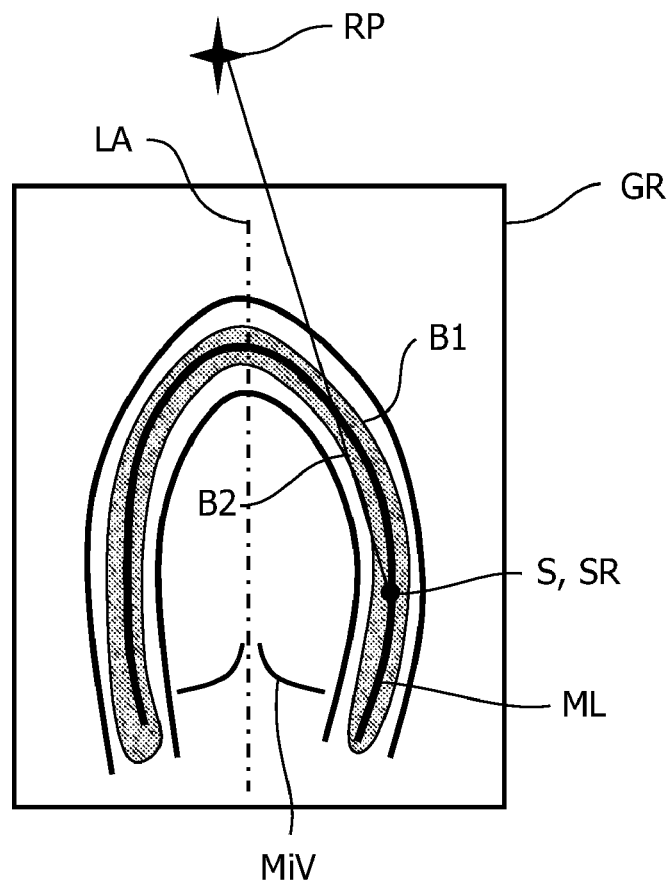
FIGS. 5A and 5B are schematical drawings of a motion vector field and corresponding projected tissue velocity values in accordance with the third and fourth embodiments of the invention.

In a fourth embodiment of the invention shown in FIG. 5A, the system in accordance with the invention comprise means for selecting a first and a second border $B_1$, $B_2$ within the 3D image data set. These first and second borders are further used to delimit a region of interest in which the deformation values S, SR have to be evaluated. In the particular case of the heart, these first and second borders are advantageously selected within the myocardium. As a matter of fact, the evaluated deformation values give information about the contraction/distension, which is directly related to the activity of the myocardium. On the contrary, there are regions, like, for example, the heart cavities, which are filled with blood and for which the velocity and deformation information is not very relevant. It may even constitute a source of noise and perturbation for analysing the deformations values calculated for the neighbouring regions.

Referring to FIG. 5A, the graphical representation GR produced by the display means 10 only render the deformation values within the region of interest delimited by the first and second borders $B_1$, $B_2$. Therefore, a first advantage of the fourth embodiment of the invention is to provide deformation evaluation only for the relevant regions of interest. A second advantage of delimiting the regions of interest is to reduce the computation cost.

Such a selection may be performed manually by choosing image data points of the first and second borders on a grey-level representation of the 3D image data point. Alternatively, this selection could consist in an image segmentation of the epicardial and endocardial walls, by using well-known image processing techniques in a semi-automatic or automatic way.

The graphical representation shown in FIG. 5A only represents the deformation values corresponding to image data points of the region of interest intersecting the view plane VP. It should be noted however that any 3D graphical representation of the region of interest is comprised within the scope of the present invention.

In a fifth embodiment of the invention, the reference point RP may also be chosen inside the 3D image data set. In this case, the drawn scanlines SL do not correspond to the paths of ultrasonic beams fired by a real probe, because the probe is generally not placed within the heart, but outside the patient body on the skin surface.

Figure 5B:
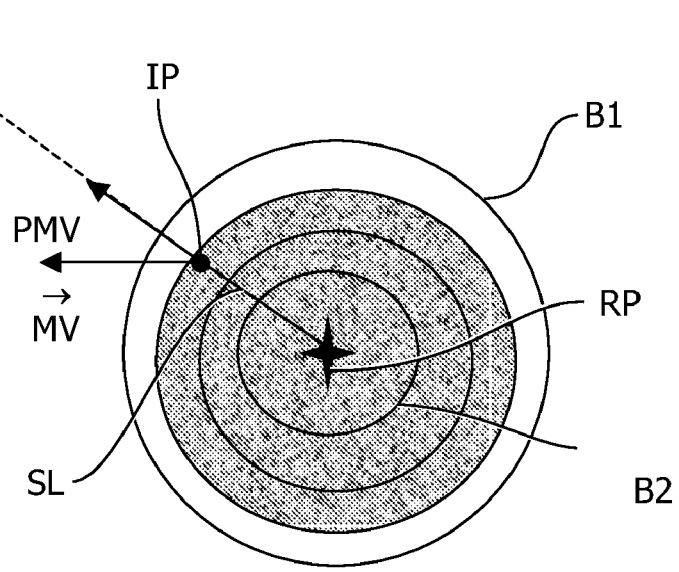

Referring to FIG. 5B, the reference point and the view plane VP may be chosen such that a radial short-axis view of the heart is obtained. To this end, the reference point belongs to the long axis of the heart. In addition, relevant anatomical references are the long axis LA and the mitral valves MiV shown in FIG. 6A. In particular, the chosen view is perpendicular to the long axis and intersects? the long axis at the reference point location beyond the mitral valves. The projected motion values and the corresponding deformation values S, SR are then calculated for the image data points included in said short axis view plane.

Advantageously, the calculation of the deformation values may be restricted to a region of interest defined by a first and a second border $B_1$, $B_2$.

An advantage of the fifth embodiment of the invention is that a radial component of the deformation is calculated. This is of great interest because this radial component of the deformation can be made to correspond with the internal structure of the myocardium, and in particular with the way in which the muscular fibers of the myocardium are expected to get contracted.

Figure 6:
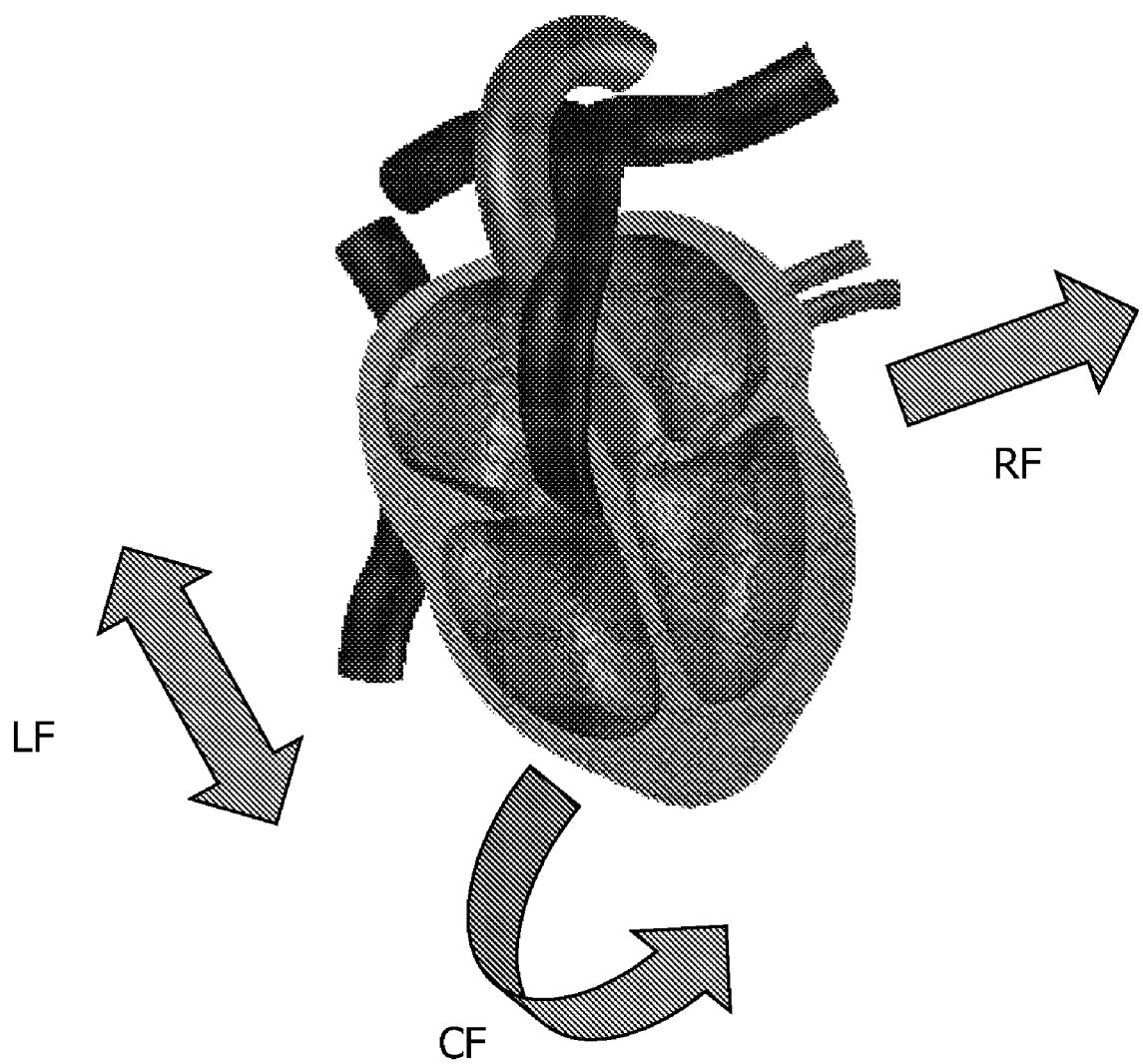
FIG. 6 is a schematical drawing of the components of the myocardial contraction.

Referring to FIG. 6, the contraction of the myocardium is governed by three main contraction forces: a longitudinal force LF induces a longitudinal motion along the long axis of the heart; a radial force RF induces a radial motion of the tissue, which causes the width of the myocardial wall to vary during the cardiac cycle; and a circumferential force induces a torsion of the myocardium with respect to the long axis.

With classical TDI techniques, only the longitudinal component of the myocardial contraction can be characterized from an apical acquisition. As a consequence, an advantage of the fifth embodiment of the invention is to isolate and to quantitatively assess both the longitudinal and radial components of the myocardial contraction with one single acquisition.

In a sixth embodiment of the invention, a second graphical representation is generated from a second reference point and, advantageously, a second view plane. From this second reference point, a second set of 1D components of the deformation is obtained from the previously calculated motion vectors simply by recalculating new projected motion values and deformation values from said second reference point. It should be noted that this sequence of operations can be repeated as many times as required. An advantage is that the system in accordance with the sixth embodiment allows the generation of a plurality of graphical representations of 1D components of the deformation of the body organ from a single ultrasonic acquisition. These 1D components of the tissue deformation, for example the radial, longitudinal, and circumferential components of the heart deformation, can advantageously be visualized at the same time for providing the user with a graphic and quantitative representation of the deformation of the body organ from a plurality of points of view.

Figure 7A:
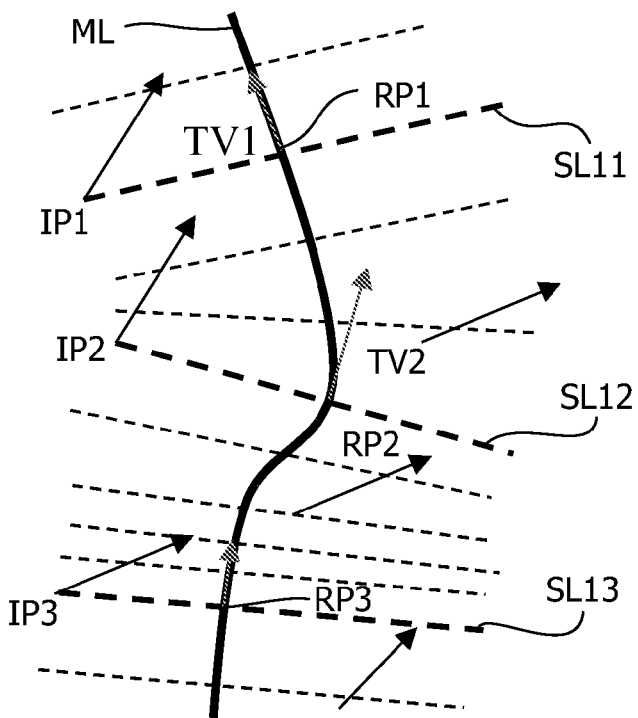
FIGS. 7A and 7B are examples of graphical representations of the evaluated tissue deformation in accordance with the fifth and sixth embodiments of the invention.
Figure 7B:
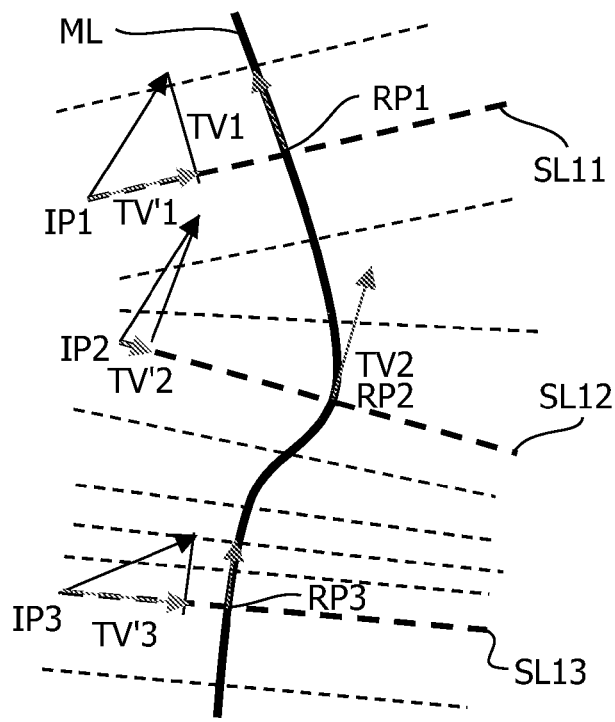

In a seventh embodiment of the invention, a specific reference point is selected for a image data point for which a motion vector has been calculated. Referring to FIGS. 7A and 7B, a curved line ML is defined between the first and second borders $B_1$, $B_2$ that have been selected within the body organ. Said curved line ML is designed to comprise the reference points $RP_i$ corresponding to the image data points $IP_i$, where i is an integer. The reference point $RP_i$ is selected on the curved line ML such that the first scanline $SL_1(IP_i)$ linking the image data point $IP_i$ to the reference point $RP_i$ is perpendicular to a tangent of said curved line ML at said reference point $RP_i$.

An advantage of the seventh embodiment of the invention is that a curved line can be selected which follows the shape of the region of interest delimited by the first and second borders $B_1$, $B_2$. For example, the curved line ML of FIG. 7A has the local direction of the myocardium wall. Therefore, the motion vectors are projected along the first scanlines, which are perpendicular to the directions of the muscular fibers. Projected tissue velocities TV1, TV2, TV3 corresponding to the image data points $IP_1$, $IP_2$, $IP_3$ are obtained. An evaluation of the radial deformation of the myocardial wall can be derived from these projected tissue velocities, which is more reliable. As a matter of fact, the projection is performed along the exact radial direction for a given image point. In FIG. 7B, the motion vectors $\vec{MV}_1$, $\vec{MV}_2$, $\vec{MV}_3$ are projected on a second scanline $SL_2(IP_i)$, which correspond to a tangent of the curved line ML at the reference point $RP_i$. Projected tissue velocities TV'1, TV'2, TV'3 corresponding to the image data points $IP_1$, $IP_2$, $IP_3$ are obtained. A second component of the deformation $S_2$, $SR_2$ along the second scanline $SL_2$ can be derived, which exactly corresponds to a longitudinal component of the tissue deformation at the image data point $IP_i$.

Figure 8:
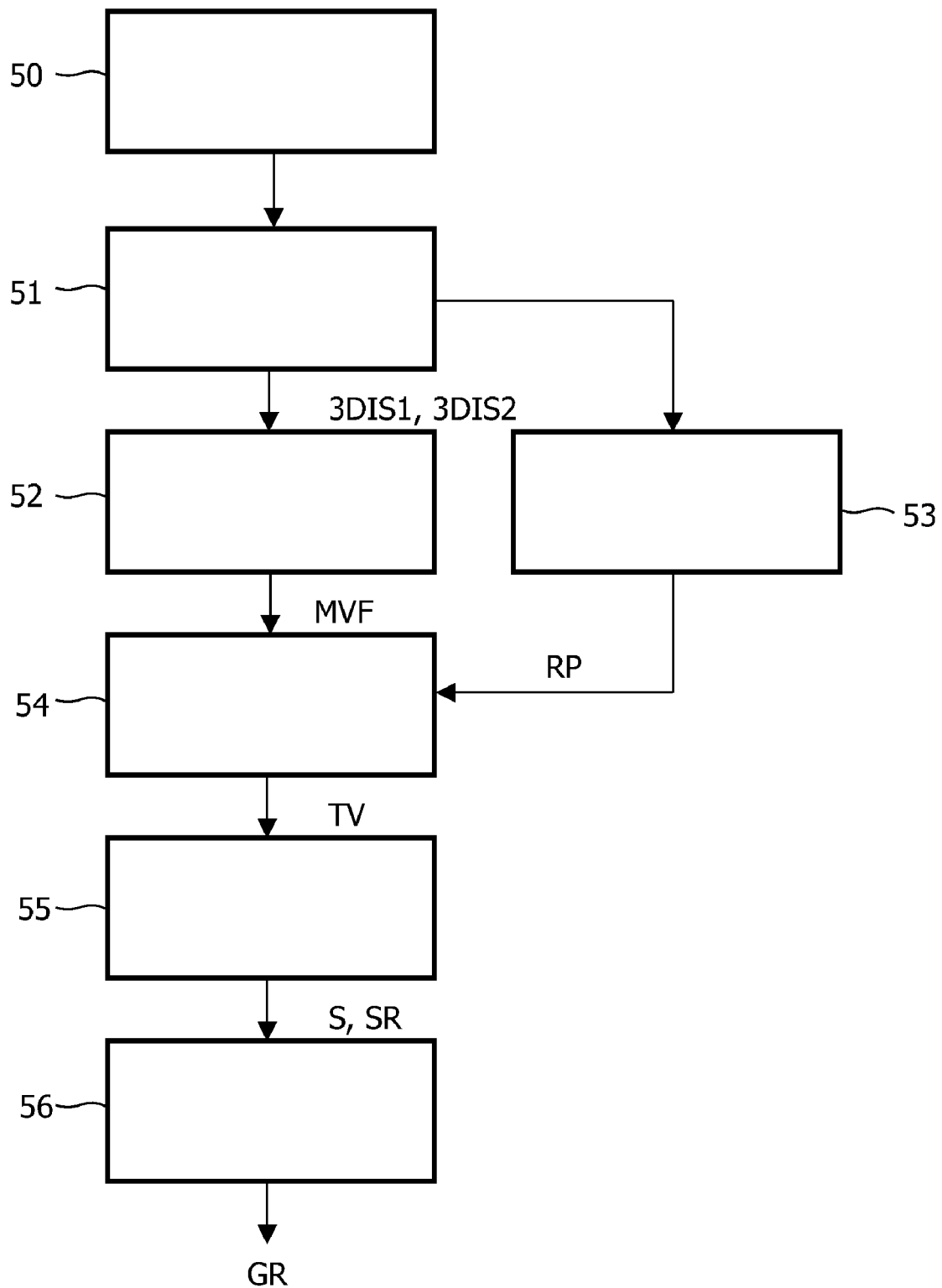
FIG. 8 is a schematical representation of an imaging method in accordance with the invention.

The schematic diagram of FIG. 8 describes in a functional way an imaging method in accordance with the invention. Such a method comprises the steps of: acquiring (51) a sequence of three-dimensional (3D) image data sets comprising at least a first 3D image data set $3DIS_1$ of echographic data and a second 3D image data set $3DIS_2$ of echographic data from said body organ by transmitting ultrasonic beams against said body organ and receiving corresponding beams reflected by said body organ;

calculating (52) a motion vectors $\vec{MV}$ corresponding to an image data point IP of said sequence of 3D image data sets between said second 3D image data set and said first 3D image data set, said image data point comprising coordinates I(x, y, z) within a referential of said sequence of 3D image data sets; selecting (53) a reference point RP within said referential of said second sequence of 3D image data sets, projecting (54) said motion vector $\vec{MV}$ to a first scanline SL which links said image data point to said reference point RP, said means being configured to generate a projected tissue velocity value TV;

evaluating (55) a deformation value S, SR of the tissue at said image data point IP through calculation of a spatial gradient of said projected tissue velocity value TV.

producing (56) and displaying a graphical representation GR of said deformation value.

The drawings and their description hereinbefore illustrate rather than limit the invention. It will be evident that there are numerous alternatives which fall within the scope of the appended claims. In this respect the following closing remarks are made: there are numerous ways of implementing functions by means of items of hardware or software, or both. In this respect, the drawings are very diagrammatic, each representing only one possible embodiment of the invention. Thus, although a drawing may show different functions as different blocks, this by no means excludes that a single item of hardware or software carries out several functions, nor does it exclude that a single function is carried out by an assembly of items of hardware or software, or both.

Any reference sign in a claim should not be construed as limiting the claim. The use of the verb "to comprise" and its conjugations does not exclude the presence of elements or steps other than those stated in a claim. The use of the article "a" or "an" preceding an element or step does not exclude the presence of a plurality of such elements or steps.

The invention claimed is:

1. An ultrasonic imaging system for evaluating and displaying a deformation of a body organ, comprising:
an ultrasonic probe configured to acquire a sequence of image data sets comprising at least a first image data set of echographic data and a second image data set of echographic data from said body organ by transmitting ultrasonic beams against said body organ and receiving corresponding beams reflected by said body organ; and
a processor including a computer program therein configured to:
calculate motion vectors corresponding to image data points of said sequence of image data sets between said second image data set and said first image data set, said image data points comprising coordinates within a referential of said sequence of image data sets;
select a reference point within said referential of said sequence of image data sets;
project a motion vector corresponding to an image data point onto a first scanline which links said image data point to said reference point to generate a first projected tissue velocity value of the body organ at said image data point;
project said motion vector onto a second scanline, which second scanline, for said image data point, is perpendicular to the first scanline to generate a second projected tissue velocity value of the body organ at said image data point;
derive an evaluation of two components of a deformation of the body organ at said image data point from said two projected tissue velocity values; and
display a graphical representation of said deformation.

2. The ultrasonic imaging system of claim 1, wherein deriving the evaluation of the deformation of the body organ further comprises evaluating a strain rate by calculating a spatial gradient of said projected tissue velocity value or strain, which is obtained by integrating the strain rate over time.

3. The ultrasonic imaging system of claim 1, wherein the sequence of image data sets is a sequence of 3D image data sets.

4. The ultrasonic imaging system of claim 3, wherein the processor is further configured to select a view plane within said 3D image data sets, said view plane including said reference point.

5. The ultrasonic imaging system of claim 4, wherein selecting the view plane further comprises identifying anatomical reference points in the 3D image data sets, wherein said anatomical reference points are used for defining said view plane.

6. The ultrasonic imaging system of claim 5, wherein displaying the graphical representation of the deformation further comprises displaying the evaluation of the deformation of the image data points which are included in said view plane.

7. The ultrasonic imaging system of claim 5, wherein said body organ is a heart, and said anatomical reference points comprise points belonging to a long axis of the heart and its apex.

8. The ultrasonic imaging system of claim 5, wherein said body organ is a heart, and said anatomical reference points comprise points belonging to a short axis of the heart and its mitral valves.

9. The ultrasonic imaging system of claim 1, wherein the processor is further configured to select a first and a second border within the sequence of image data sets, wherein displaying the graphical representation further comprises displaying the evaluations of deformations of the image data points which are localized between said first and second borders.

10. The ultrasonic imaging system of claim 9, wherein the processor is further configured to select a curved line ML between said first and second borders and wherein the selecting the reference point is further configured to select a reference point which belongs to said curved line, such that a first scanline $SL_1$ linking the image data point to the reference point is perpendicular to a tangent of said curved line at said reference point.

11. An ultrasonic imaging method for visualizing deformation of tissues of a body organ, comprising the steps of:
    acquiring a sequence of image data sets comprising at least a first image data set of echographic data and a second image data set of echographic data from said body organ by transmitting ultrasonic beams against said body organ and receiving corresponding beams reflected by said body organ;
    calculating motion vectors corresponding to image data points of said sequence of image data sets between said second image data set and said first image data set, said image data points comprising coordinates within a referential of said sequence of image data sets;
    selecting a reference point within said referential of said sequence of image data sets;
    projecting motion vectors of image data points onto first scanlines which link said image data points to said reference point, to generate first projected tissue velocity values of said body organ at said image data points;
    projecting each motion vector onto a second scanline, which second scanline, for each image data point, is perpendicular to the first scanline to generate a second projected tissue velocity value of the body organ at said image data point;
    evaluating a deformation value of tissue at said image data point through calculation of a spatial gradient of each of said projected tissue velocity values; and
    displaying a graphical representation of said deformation value.

* * * * *